US00PP20289P2

(12) United States Plant Patent
Saul

(10) Patent No.: US PP20,289 P2
(45) Date of Patent: Sep. 8, 2009

(54) ***VINCA* PLANT NAMED '24 CARAT'**

(50) Latin Name: *Vinca minor*
Varietal Denomination: 24 Carat

(75) Inventor: Richard Saul, Cleveland, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 0 days.

(21) Appl. No.: 12/215,882

(22) Filed: Jun. 30, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Vinca* plant named '24 Carat', characterized by its compact, outwardly spreading to trailing plant habit; short internodes; densely foliated habit; strong and healthy leaves; developing leaves that are yellow in color becoming green with development; and good garden performance.

1 Drawing Sheet

Botanical designation: *Vinca minor.*
Cultivar denomination: '24 Carat'.

BACKGROUND OF THE INVENTION

The present invention relates to a new and distinct cultivar of *Vinca,* botanically known as *Vinca minor* and hereinafter referred to by the name '24 Carat'.

The new *Vinca* is a naturally-occurring branch mutation of an unnamed selection of *Vinca minor,* not patented. The new *Vinca* was discovered and selected by the Inventor from within a population of plants of the parent selection in a controlled greenhouse environment in Dahlonega, Ga. in June, 2002.

Asexual reproduction of the new *Vinca* by vegetative cuttings in a controlled greenhouse environment in Dahlonega, Ga. since July, 2002, has shown that the unique features of this new *Vinca* are stable and reproduced true to type in successive generations.

SUMMARY OF THE INVENTION

Plants of the new *Vinca* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of '24 Carat'. These characteristics in combination distinguish '24 Carat' as a new and distinct cultivar of *Vinca:*

1. Compact, outwardly spreading to trailing plant habit.
2. Short internodes; densely foliated.
3. Strong and healthy leaves.
4. Developing leaves yellow in color becoming green with development.
5. Good garden performance.

Plants of the new *Vinca* differ primarily from plants of the parent selection in the following characteristics:

1. Plants of the new *Vinca* are not as vigorous as plants of the parent selection.
2. Developing leaves of plants of the new *Vinca* are yellow in color whereas developing leaves of plants of the parent selection are green in color.

Plants of the new *Vinca* can be compared to plants of *Vinca minor* 'Sunny Skies', disclosed in U.S. Plant Pat. No. 13,466. Plants of the new *Vinca* and 'Sunny Skies' differ in the following characteristics:

1. Plants of the new *Vinca* are not as upright as plants of 'Sunny Skies'.
2. Plants of the new *Vinca* and 'Sunny Skies' differ in leaf color as plants of 'Sunny Skies' have golden yellow green and dark green-variegated leaves.

BRIEF DESCRIPTION OF THE PHOTOGRAPH

The accompanying colored photograph illustrates the overall appearance of the new *Vinca,* showing the colors as true as it is reasonably possible to obtain in colored reproductions of this type. Colors in the photograph may differ slightly from the color values cited in the detailed botanical description which accurately describe the colors of the new *Vinca.* The photograph comprises a top perspective view of a typical plant of '24 Carat' grown in an outdoor nursery.

DETAILED BOTANICAL DESCRIPTION

The aforementioned photograph and following observations, measurements and values describe plants grown during the spring and summer in an outdoor nursery in Tolar, Tex. Plants had been growing for a year in the outdoor nursery when the photograph and description were taken. In the following description, color references are made to The Royal Horticultural Society Colour Chart, 1995 Edition, except where general terms of ordinary dictionary significance are used.

Botanical classification: *Vinca minor* '24 Carat'.
Parentage: Naturally-occurring branch mutation of an unnamed selection of *Vinca minor,* not patented.

Propagation:

*Type.*—By vegetative cuttings.

*Time to initiate roots, summer.*—About two weeks at 21° C. to 27° C.

*Time to initiate roots, winter.*—About three to four weeks at 27° C. to 32° C.

*Time to produce a rooted young plant, summer.*—About four to five weeks at 21° C. to 27° C.

*Time to produce a rooted young plant, winter.*—About six to eight weeks at 24° C.

*Root description.*—Fibrous; medium in thickness; color, close to 7B.

*Rooting habit.*—Moderately branching; moderately dense.

Plant description:

*Plant form and growth habit.*—Compact, outwardly spreading to trailing plant habit; herbaceous, woody-based perennial subshrub. Short internodes; densely foliated. Moderately vigorous growth rate.

*Branching habit.*—Freely basal branching habit, usually about ten to twelve basal branches develop per plant.

*Plant height.*—About 6 cm.

*Plant diameter.*—About 37 cm.

*Basal branch description.*—Length: About 35 cm. Diameter: About 1.5 cm. Internode length: About 2 mm. Strength: Strong. Texture: Smooth, glabrous. Color, developing stems: Close to 147C flushed with close to 187B; color becoming closer to 10C with development. Color, older stems: Close to 147C.

*Leaf description.*—Arrangement: Opposite; simple; strong and healthy leaves. Length: About 2.75 cm. Width: About 2 cm. Shape: Ovate. Apex: Acute. Base: Obtuse. Margin: Entire. Texture, upper and lower surfaces: Smooth, glabrous; thick; waxy. Venation: Pinnate. Color: Developing leaves, upper surface: Close to 7A. Developing leaves, lower surface: Close to 8C. Fully expanded leaves, upper surface: Close to 137A; venation, close to 137A. Fully expanded leaves, lower surface: Close to 147B; venation, close to 147B. Petiole: Length: About 5 mm. Diameter: About 1 mm. Texture, upper and lower surfaces: Smooth, glabrous. Color, developing leaves, upper and lower surfaces: Close to 148C, flushed with close to 187B. Color, fully expanded leaves, upper and lower surfaces: Close to 148C.

Flower description: Flower development as not been observed on plants of the new *Vinca*.

Disease/pest resistance: Plants of the new *Vinca* have not been observed to be resistant to pathogens and pests common to *Vinca*.

Garden performance: Plants of the new *Vinca* have been observed to have good garden performance and tolerate rain, wind and temperatures ranging from about −20° C. to about 40° C.

It is claimed:

1. A new and distinct *Vinca* plant named '24 Carat' as illustrated and described.

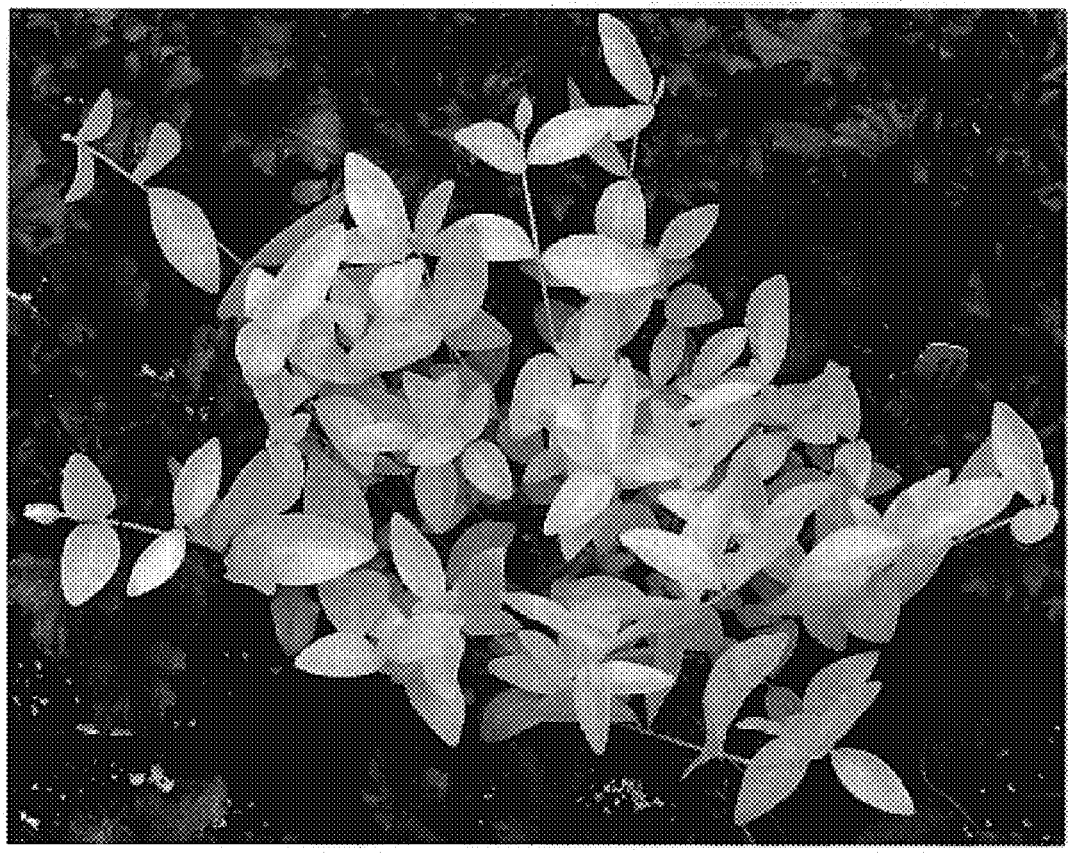

* * * * *